United States Patent
Betageri et al.

[11] Patent Number: 6,156,784
[45] Date of Patent: Dec. 5, 2000

[54] COMPOUNDS USEFUL AS PHOSPHOTYROSINE MIMICS

[75] Inventors: Rajashekhar Betageri, Bethel, Conn.; Jean-Marie Ferland, St. Laurent; Montse Llinas-Brunet, Dollard-des-Ormeaux, both of Canada; Neil Moss, Ridgefield; John R. Proudfoot, Newtown, both of Conn.

[73] Assignee: Boehringer Ingelheim Pharmaceuticals, Inc., Ridgefield, Conn.

[21] Appl. No.: 09/455,633

[22] Filed: Dec. 7, 1999

Related U.S. Application Data

[63] Continuation-in-part of application No. 09/208,113, Dec. 9, 1998.
[60] Provisional application No. 60/129,414, Apr. 15, 1999, and provisional application No. 60/069,971, Dec. 18, 1997.
[51] Int. Cl.$^7$ .................. A61K 31/40; A61K 31/215; A61K 31/185; C07C 229/04
[52] U.S. Cl. ............... 514/426; 514/427; 514/506; 514/553; 514/708; 548/557; 548/560; 548/561; 548/565; 560/19; 560/37; 560/55; 560/76; 562/443
[58] Field of Search ............... 560/19, 37, 55, 560/76; 514/740, 784, 785, 506, 553, 426, 427, 708; 562/443; 548/557, 560, 561, 565

[56] References Cited

U.S. PATENT DOCUMENTS

| | | |
|---|---|---|
| 5,200,546 | 4/1993 | Burke, Jr. et al. . |
| 5,580,979 | 12/1996 | Bachovchin . |
| 5,891,912 | 4/1999 | Kawashima et al. .................. 514/33 |

FOREIGN PATENT DOCUMENTS

| | | |
|---|---|---|
| 0 727 211 A1 | 8/1996 | European Pat. Off. . |
| WO 95/25118 | 9/1995 | WIPO . |
| 9614293 | 5/1996 | WIPO . |
| WO 96/23813 | 8/1996 | WIPO . |
| WO 96/30332 | 10/1996 | WIPO . |
| WO 97/12903 | 4/1997 | WIPO . |
| WO 97/31016 | 8/1997 | WIPO . |
| 9742501 | 11/1997 | WIPO . |
| WO 97/42501 | 11/1997 | WIPO . |

OTHER PUBLICATIONS

Songyang, Zhou et al; SH2 Domains Recognize Specific Phosphopeptide Sequences, Cell. vol. 72, 767–773, Mar. 12, 1993.

Gilmer, T. et al; Peptide Inhibitors of src SH3–SH2 Phosphoprotein Interactions, The Journal of Biological Chemistry vol. 269, No. 50 Issue of Dec. 16, pp. 31711–31719.

Ye, Bin et al; L–0–(2–Malonyl)tyrosine: a New Phosphotyrosyl Mimetic for the Preparation of Src Homology 2 Domain Inhibitory Peptides, J. Med. Chem. 1995, 38, 4270–4275.

Burke, Terrence R. Jr. et al; Conformationally Constrained Phosphotyrosyl Mimetics Designed as Monomeric Src Homology 2 Domain Inhibitors, J. Med. Chem. 1995, 38, 1386–1396.

Wange, Ronald J. et al; $F_2(Pmp(_2-TAM \zeta_3$ a Novel Competitive Inhibitor of the Binding of ZAP–70 to the T Cell Antigen Receptor, Blocks Early T Cell Signaling.

Shahripour, A.. et al; Design, Synthesis and Structure Activity Studies of Peptidomimetic Ligands Targeting the pp60 src SH2 Domain, Parke–Davis, $221^{th}$ ACS National Meeting Mar. 1996, Poster #194.

Para, K.S. et al; Design of Novel Peptidomimetic Ligands Targeting the pp60srcSH2 Domain: Transposed Sidechain and Rigid Scaffold Modifications, Parke–Davis, $211^{th}$ ACS National Meeting Mar. 1996, Poster #195.

Jian Min Fu; Design and Synthesis of a Pyridone–Based Phosphotyrosine Mimetic, XP–002101974, Bioorganic & Medicinal Chemistry Letters 8, (1998), 2813–2816.

Zhu–Jun Yao, et al; Potent Inhibition of Grb2 SH2 Domain Binding by Non–Phosphate–Containing Ligands J. of Med, Chem., vol. 32, No. 1, 1999, pp. 25–35, XP002138438.

Lai J.H. et al; "The Design, Synthesis and Activity of Pentape ptide PP60C–SRC Inhibitors Containing L–Phosphotyrosine Mimics", J. of Peptide Research, DD. Munksgaard International Publishers, Copenhagen, vol. 51, No. 4., Apr. 1, 1998 (Apr. 1, 1998) pp. 271–181, XP00736419, SSN1307–002X.

International Search Report for International Application No. PCT/US 99/27757.

Caplus 128:32126, abstract RN#'s 199526–77–7 and 199526–79–9, Nov. 1997.

Caplus 124:176907, Int. J. Pept. Protein Res. 1995 vol. 46 (6) pp. 535–546.

USpatfull 1999: 43656; RN #'s 179177–31–2, May 1996.

*Primary Examiner*—John Kight
*Assistant Examiner*—Rita Desai
*Attorney, Agent, or Firm*—Robert P. Raymond; Anthony P. Bottino; Alan R. Stempel

[57] ABSTRACT

Disclosed are compositions containing compounds of the formula (I) below wherein A,B,C,G,Q and R are defined herein. The compounds are useful as phosphotyrosine mimics that, when incorporated into an appropriate molecular structure, inhibit the binding of tyrosine kinase-dependent regulatory proteins to their native phosphotyrosine-containing ligands or receptors. Also disclosed are methods for preparing the compounds of the formula (I).

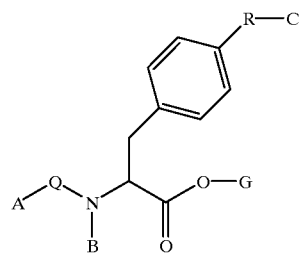

10 Claims, No Drawings

COMPOUNDS USEFUL AS PHOSPHOTYROSINE MIMICS

RELATED APPLICATION DATA

This Application claims benefit to U.S. Provisional Application Ser. No.60/129,414, filed Apr. 15, 1999, and is a continuation-in-part of U.S. application Ser. No. 09/208,113, filed Dec. 9, 1998 which claims benefit to U.S. Provisional Ser. No. 60/069,971, filed Dec. 18, 1997.

TECHNICAL FIELD OF INVENTION

This invention relates to phosphotyrosine mimics which, when incorporated into an appropriate molecular structure, are capable of inhibiting the binding of tyrosine kinase-dependent regulatory proteins to their native phosphotyrosine—containing ligands or receptors. The compounds of this invention are useful for designing antagonists of tyrosine-kinase dependent regulatory proteins, such as signal transduction proteins containing $SH_2$ binding domains.

BACKGROUND OF THE INVENTION

The activation of cells by growth factors, mitogens or other cytokines to undergo proliferation and/or differentiation is often dependent on inducible tyrosine kinase activity. This tyrosine kinase activity increases the phosphotyrosine content of many receptor-like and cytoplasmic regulatory proteins. Often, the physical association of such regulatory proteins is mediated through those phosphotyrosine residues.

For example, one mechanism of cellular regulation involves the physical association of signal transduction proteins with one or more phosphorylated tyrosine-containing receptor subunits, called immunoreceptor tyrosine-based activation motifs (ITAMs), present on its native ligand or receptor. This association is a common feature of many cytoplasmic signal transduction pathways, as well as other immunologically important regulatory protein-receptor based interactions (M. A. Osborne et al., *Bio Technoloy,* 13 (1995)). Of particular importance is the interaction between phosphorylated ITAMs and regulatory proteins containing Src homology domain 2 regions ("$SH_2$ binding domains"). Examples of immunologically important proteins containing $SH_2$ binding domains include ZAP-70, Fyn, Lyn, Lnk, Abl, Vav, Huk, Blk, PLCγγl, GAP, Crk, Shc and p[56]lck. Although proteins having $SH_2$ binding domains tend to have sequence-specific affinities for their ITAM containing ligands or receptors, the binding interaction itself is ubiquitously mediated through one or more phosphorylated tyrosine residues. Therefore, the presence of phosphorylated tyrosine plays a critical role in signal transduction involving virtually all proteins containing $SH_2$ binding domains.

Given the above understanding of signal transduction and cellular regulation, it follows that growth factor- and cytokine-induced cell proliferation and/or differentiation can be selectively inhibited by antagonizing the interaction of regulatory proteins dependent on tyrosine kinase activity with their native phosphotyrosine-containing ligands or receptors. Such antagonists would undoubtedly be useful to treat a variety of disorders, including those associated with or caused by neoplastic diseases or chronic inflammatory diseases.

To date, however, antagonists of tyrosine kinase-dependent regulatory proteins have not fulfilled their potential as useful pharmaceutical agents. One major hurdle has been the necessary inclusion of a phosphorylated α-amino acid residue or a phosphorylated analog thereof, to perform the crucial role of the native tyrosine phosphoprotein ligands or receptors of these regulatory proteins. However, agents containing phosphotyrosine, other phosphorylated α-amino acid residues, or phosphorylated analogs thereof, cannot generally be used as therapeutic agents because the presence of the phosphorylated moiety substantially impedes cell penetrability. Until now, no effective replacement or mimic for the critical phosphotyrosine residue has been identified. Accordingly, the need exists for effective phosphotyrosine mimics.

SUMMARY OF THE INVENTION

This invention satisfies the above-mentioned needs by providing compositions containing phosphotyrosine mimic compounds of the formula (I):

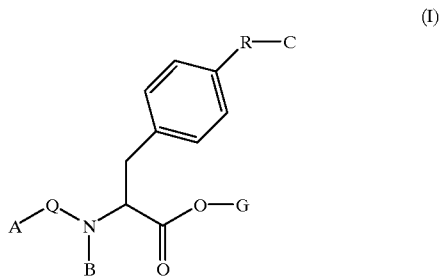

wherein A,B,C,G,Q and R are defined herein.

It is therefore an object of this invention is to provide phosphotyrosine mimic compounds that, when incorporated into an appropriate molecular structure, inhibit the binding of tyrosine kinase-dependent regulatory proteins to their native phosphotyrosine-containing ligands or receptors.

A further object of this invention is to provide methods for using phosphotyrosine mimic compositions to treat diseases related to tyrosine kinase-dependent regulatory proteins by administering to a patient in need of such treatment an effective amount of a composition including a phosphotyrosine mimic.

Other objects and advantages of this invention will be apparent to those of ordinary skill in the art.

DETAILED DESCRIPTION OF THE INVENTION

The invention provides for phoshotyrosine mimic compounds of the formula (I):

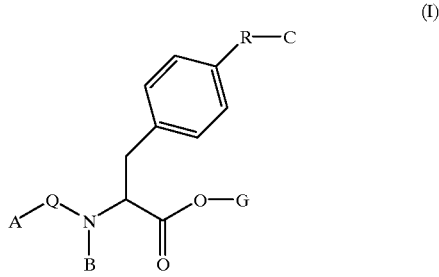

wherein:

A is selected from the group consisting of alkyl; alkenyl; alkynyl; alkoxy; cycloalkyl; cycloalkenyl; heterocyclyl and aryl; wherein said cycloalkyl, heterocyclyl or aryl is optionally linked to Q or N via an alkoxy, —O—, amino, lower alkyl, lower alkyl amino, carbonyl, amido, amido alkyl, alkoxycarbonyl, carbonylalkyloxy, cycloalkyl and heterocyclyl linker;

Q is selected from the group consisting of a bond, >C=O, >S(O)$_2$ and >C=S; wherein A and Q optionally form a nitrogen protecting group (NPG);

B is selected from the group consisting of H; lower alkyl and a nitrogen-protecting group;

G is selected from the group consisting of H or an oxygen-protecting group (OPG);

R is CR$_1$R$_2$ wherein R$_1$ is H, alkyl, or alkoxy and R$_2$ is OH, alkyl, or alkoxy, and wherein R$_1$ and R$_2$ may be connected to form a ring of between three and 6 members if R$_1$ is alkyl or alkyloxy.

C is an acid functionality that carries one negative charge at physiological pH, optionally covalently attached to an OPG or a physiologically acceptable salt or ester thereof.

A composition containing the phosphotyrosine mimic of the formula (I) is capable of inhibiting binding of tyrosine kinase-dependent regulatory proteins.

A preferable subgeneric aspect of the invention comprises the phoshotyrosine mimic compound according to invention wherein A—Q of the compound of formula (I) form a nitrogen protecting group (NPG); B is hydrogen and R is CHOH, C(CH$_3$)OH, C(CH$_3$)$_2$, C(CH$_2$CH$_3$)$_2$, cyclopropyl, cyclopentyl or CHCH$_3$.

A more preferable subgeneric aspect of the invention comprises the phoshotyrosine mimic compound according to invention wherein R is —C(CH$_3$)$_2$—, and C is a carboxyl group.

Unless otherwise indicated, the following definitions apply:

The term "alkyl" refers to a saturated aliphatic radical containing from one to ten carbon atoms. "Alkyl" refers to both branched and unbranched alkyl groups.

The term alkoxy refers to a terminal oxy containing "alkyl", as described above, preferred alkoxy groups are methoxy, ethoxy and propoxy.

The term "cycloalkyl" refers to the cyclic analog of an alkyl group, as defined above. Preferred cycloalkyl groups are saturated cycloalkyl groups containing from three to eight carbon atoms, and more preferably, three to six carbon atoms. "Alkyl" and "cycloalkyl", as used herein, include unsubstituted alkyl and cycloalkyl radicals, those radicals that are partially or fully halogenated and those radicals substituted with one to four, preferably one or two, substituents selected from halo, amino, cyano, nitro, methoxy, ethoxy and hydroxy.

The terms "alkenyl" and "alkynyl" refer to mono- or polyunsaturated aliphatic hydrocarbon radical containing from two to twelve carbon atoms, containing at least one double or triple bond, respectively. "Alkenyl" and "alkynyl" refer to both branched and unbranched alkenyl and alkynyl groups. Preferred alkenyl and alkynyl groups are straight chain alkenyl or alkynyl groups containing from two to eight carbon atoms and branched alkenyl or alkynyl groups containing from five to ten carbon atoms. More preferred alkenyl and alkynyl groups are straight chain alkenyl or alkynyl groups containing from two to six carbon atoms and branched alkenyl or alkynyl groups containing from five to eight carbon atoms. The term "cycloalkenyl" refers to the cyclic analog of an alkenyl group, as defined above. Preferred cycloalkenyls include cycloalkenyl rings containing from three to eight carbon atoms, and more preferably, from three to six carbon atoms. "Alkenyl", "alkynyl" and "cycloalkenyl", as used herein, include unsubstituted alkenyl or alkynyl radicals, those radicals that are partially or fully halogenated and those radicals substituted with one to four, preferably one or two, substituents selected from halo, amino, cyano, nitro, methoxy, ethoxy and hydroxy.

The term "aryl" refers to phenyl and naphthyl, phenyl and naphthyl that are partially or fully halogenated and phenyl and naphthyl substituted with halo, alkyl; hydroxyl; nitro; —COOH; —CO(lower alkoxy); —CO(lower alkyl); amino; alkylamino; dialkylamino; alkoxy; —NCOH; —NCO(lower alkyl); —NSO$_2$—Ph(halo)$_{0-3}$, Ph; —O—Ph; naphthyl; —O-naphthyl; pyrrolyl; pyrrolyl subsituted with lower alkyl; pyridyl; pyridinyl; pyrazinyl; pyrimidinyl and pyridazinyl. Preferred aryl groups in position A in compounds of formula (I) include unsubstituted phenyl and phenyl substituted as defined above (preferably in the para-position).

The term "halo" refers to a halogen radical selected from fluoro, chloro, bromo or iodo. Preferred halo groups are fluoro, chloro and bromo.

The terms "heterocycle" refers to a stable 5–8 membered (but preferably, 5 or 6 membered) monocyclic or 8–11 membered bicyclic heterocycle radical which may be either saturated or unsaturated, aromatic or non-aromatic, and which may be optionally benzo- or pyridofused if monocyclic. Each heterocycle consists of carbon atoms and from 1 to 4 heteroatoms selected from the groups consisting of nitrogen, oxygen and sulfur. As used herein, "nitrogen" and "sulfur" include any oxidized form of nitrogen and sulfur and the quaternized form of any basic nitrogen. The heterocycle may be attached by any atom of the cycle which results in the creation of a stable structure. Preferred heterocycles include, for example, benzimidazolyl, furazanyl; imidazolyl, imidazolinoyl, imidazolidinyl, quinolyl, isoquinolyl, indolyl, oxazolyl, pyridyl, pyrrolyl, pyrrolinyl, pyrazolyl, pyrazinyl, pyrimidinyl, pyridazinyl, quinoxolyl, piperidinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazoyl, benzodioxolyl, tetrahydrothiophenyl and sulfolanyl. Most preferred heterocycles of this invention include imidazolyl, pyridyl, pyrrolyl, pyrazolyl, piperidinyl, morpholinyl, furyl, thienyl, thiazolyl and the benzo- and pyridofused derivatives thereof. Even more preferred are pyridyl.

"Heterocyclyl" refers to unsubstituted heterocycle radicals as defined hereinabove, those radicals that are partially or fully halogenated and those radicals substituted with alkyl; hydroxyl; nitro; —COOH; —CO(lower alkoxy); —CO(lower alkyl); amino; alkylamino; dialkylamino; alkoxy; —NCOH; —NCO(lower alkyl); —NSO$_2$—Ph (halo)$_{0-3}$, Ph; —O—Ph; naphthyl; —O-naphthyl; pyrrolyl; pyrrolyl subsituted with lower alkyl; pyridyl; pyridinyl; pyrazinyl; pyrimidinyl and pyridazinyl.

The term "lower", used in conjunction with other terms (e.g., "alkyl", "alkoxy" and the like), refers to a radical containing from one to six, preferably from one to five and more preferably, from one to four carbon atoms. For example, a "lower alkyl" group is a branched or unbranched alkyl radical containing from one to five carbon atoms.

The term "nitrogen protecting group" (NPG) refers to a substituent that is capable of protecting a reactive nitrogen functional group from undesired chemical reactions. Such nitrogen protecting groups include, for example, amino protecting groups such as acyl groups (including formyl, acetyl, benzoyl and the like) and urethanyl groups (including aromatic urethanyl groups, such as carbonylbenzyloxy (Cbz) and the like, and aliphatic urethanyl groups, such as t-butoxycarbonyl (Boc) or 9-fluorenylmethoxycarbonyl (Fmoc) and the like).

The term "oxygen protecting group" (OPG) refers to a substituent that is capable of protecting a reactive oxygen functional group from undesired chemical reactions. Such oxygen protecting groups include, for example, carboxylic acid protecting groups such as ester groups (including methyl, ethyl, $^t$butyl, benzyl, trimethylsilylethyl and the like).

The terms "amino acid" and "α-amino acid" are used interchangeably herein and refer to the naturally occurring α-amino acids, as well as those amino acids in their D-configurations and non-native, synthetic and modified amino acids known to those of ordinary skill in the art (e.g., homocysteine, ornithine, norleucine and β-valine).

The term "patient" refers to a warm-blooded animal, such as a human, who is afflicted with a neoplastic or chronic inflammatory disorder.

The term "phosphotyrosine mimic" refers to a non-phosphorylated chemical moiety which is functionally capable of replacing phosphotyrosine in a native phosphotyrosine-containing ligand.

The terms "phosphotyrosine mimic-containing compound" and "compositions" according to the invention are used interchangeably and shall be understood to mean the phosphotyrosine mimic being incorporated into an appropriate molecular structure examples of which are discussed below.

A phosphotyrosine mimic composition is capable of antagonizing the binding of a tyrosine kinase dependent regulatory protein to its natural ligand(s). The antagonistic ability of such compounds may be detected by any of the detection methods described herein, or any other conventional detection method known to those of ordinary skill in the art.

Preferably, a phosphotyrosine mimic-containing compound according to this invention is capable of inhibiting the binding of a tyrosine kinase-dependent regulatory protein to its corresponding, phosphorylated ligand or receptor by at least about 30% at a concentration of 10 μM (more preferably, by at least about 35%, even more preferably, by at least about 40%, even more preferably, by at least about 50% and most preferably, by at least 60%, 70% or even 80%).

Preferred phosphotyrosine mimic-containing compounds according to this invention are characterized by improved cell penetrability over that possessed by the corresponding phosphotyrosine-containing analogs. The improved cell penetrability possessed by these compounds advantageously allows the compounds to more readily pass through the cell membrane, thereby increasing the likelihood of physical interaction with the targeted regulatory protein (such as a particular targeted phosphotyrosine kinase-dependent regulatory protein containing an $SH_2$ binding domain).

Methods of identifying and designing phosphotyrosine mimic-containing compounds according to this invention will be apparent to those skilled in the art.

The preferred methods for identifying and designing phosphotyrosine mimic-containing compounds of this invention employ assays which measure SH2 domain binding affinity of a non-phosphorylated test compound versus a phosphotyrosine-containing substance. Although all assays that perform this function are contemplated by this invention, direct binding assays are less preferred because they tend to be difficult to carry out in a high-throughput manner. Competitive binding assays are preferred because they are more easily and quickly performed with a large number of non-phosphorylated test compounds. Many such competitive binding assays are well known to those of ordinary skill in the art. Competitive binding assays which may be used in the methods of this invention are typically immunoassays that detect the presence or concentration of the free or bound forms of SH2 domain, phosphotyrosine-containing substance or non-phosphorylated test compound. Depending on precisely which immunoassay is used, the free- and bound-forms of those substances may be readily distinguished using an appropriate label.

Particularly preferred competitive binding assays useful in the methods of this invention include, but are not limited to, enzyme-linked, fluorescent, chemiluminescent, and radio-immunoassays and biosensor assays. Although the immunoassays of this invention may be carried out in solution or on a solid support, we prefer using a solid support (such as the wells of a microtiter plate) to facilitate large-scale screening of non-phosphorylated test compounds. Preferably, the assay used in the methods of this invention is ELISA, a fluorescent immunoassay or a biosensor assay.

In an enzyme-linked immunosorbent assay (ELISA) according to this invention, the known phosphotyrosine-containing substance or the SH2 domain may be directly labeled with an enzyme or indirectly labeled with an enzyme-labeled antibody. The enzyme labels useful for ELISA are those that, under appropriate conditions, catalyze an observable reaction with a given enzymatic substrate. Such enzymatic activity is typically measured by formation of a colored or otherwise easily identifiable reaction product. In a typical ELISA scheme according to this invention, the unlabeled compound (either the known phosphotyrosine-containing substance or the SH2 domain) is bound to a solid support and the correspondingly labeled substrate is added. After any unbound species are washed away, the non-phosphorylated test compound is added. Unbound species are again removed by washing and the enzyme is activated to determine the extent to which the test compound displaced the known phosphotyrosine-containing substance. Wherever the phosphotyrosine-containing substance was displaced, no enzymatic activity will be detected.

Fluorescent immunoassays useful in the methods of this invention involve the use of conventional fluorochromes. Such fluorochromes may be linked directly to the SH2 domain or the known ligand used in the immunoassay, or alternatively, the fluorochrome may be linked indirectly to those compounds with fluorochrome-labeled antibodies.

Fluorochromes are dyes that absorb radiation (such as UV light) and emit light of a different characteristic frequency when the labeled compound is bound to a substrate or present in its free state. Therefore, when a known phosphotyrosine-containing substance according to this invention is labeled with a fluorochrome, and the SH2 domain and non-phosphorylated test compound are subsequently added, it is a routine matter to detect the extent to which the known phosphotyrosine-containing substance has been displaced by the test compound (e.g., by measuring the amount of free, known phosphotyrosine-containing substance).

In biosensor immunoassays, the binding of an SH2 domain to a known phosphotyrosine-containing substance is detected by measuring the change in refractive index that occurs when the solution-phase antibody binds to the known phosphotyrosine-containing substance which has been tethered to an optically sensitive surface. The biosensor allows the determination of equilibrium binding constants together with on and off rates of the interacting molecules. Therefore, when a known phosphotyrosine-containing substance is bound to an optically sensitive surface and the SH2 domain and non-phosphorylated test compound are subsequently added, it is a routine matter to detect the extent to which the binding of the SH2 domain to the known phosphotyrosine-containing substance has been displaced by the test compound.

Using the methods provided above, phosphotyrosine mimic containing compounds which inhibit the binding of tyrosine kinase-dependent regulatory proteins to their native receptors can be quickly and effectively assayed. Accordingly, this invention also provides a method for inhibiting the activation of a tyrosine kinase-dependent regulatory protein comprising the steps of:

(a) incorporating a phosphotyrosine mimic according to this invention into an appropriate molecular structure to produce a phosphotyrosine mimic containing compound, and (b) contacting the compound of step (a) with a tyrosine-kinase dependent regulatory protein.

An example of an appropriate molecular structure for the above detailed use is a phosphotyrosine-containing peptide or peptidomimetic in which the phosphotyrosine can be replaced with a phosphotyrosine mimic. Examples of such peptides can be found in U.S. application Ser. No. 08/852,042, incorporated herein by reference in its entirety. Preferably, the peptide or peptidomimetic comprises a fragment of a native tyrosine kinase-dependent regulatory protein ligand or receptor, in which the naturally occurring phosphotyrosine residue is replaced with a phosphotyrosine mimic identified by the methods of this invention. Such peptides or peptidomimetics generally include from about 1 to about 30 of the naturally occurring α-amino acid residues flanking each side of the naturally occurring phosphotyrosine residue. More preferably, the peptide or peptidomimetic comprises from about 1 to about 10 (and most preferably, from about 1 to about 5) of the naturally occurring α-amino acid residues flanking each side of the naturally occurring phosphotyrosine residue. Although the naturally occurring α-amino acids are preferred in these peptides or peptidomimetics, those naturally occurring α-amino acids may be optionally modified or substituted according to known techniques. Preferred modifications and substitutions to the naturally occurring amino acid sequence are conservative ones (i.e., those having a minimal influence on the secondary structure and hydropathic nature of the peptide). These include those substitutions and modification described in Dayhoff, *Atlas of Protein Sequence and Structure*, 5 (1978) and Argos, *EMBO J.*, 8, pp. 779–85 (1989).

The above described peptides or peptidomimetics may be prepared using any conventional peptide production methodology including solid phase or solution phase synthesis, and combinations thereof. Preferably, these peptides or peptidomimetics are produced using solid phase synthesis. The solid support may be any suitable resin conventionally employed in the art. Preferred resins include, but are not limited to p-benzyloxyalcohol polystyrene and p-methylbenzhydrylamine. Amino acids for use in this method may be side chain protected, if necessary. The criteria for choosing an appropriate side chain protecting group include: (a) stability of the side chain protecting group to the reaction conditions needed for removal of the α-amino protecting group, (b) stability of the side chain protecting group to the reaction conditions required for amino acid coupling and (c) removability of the side chain protecting group upon the conclusion of pepticle synthesis and under conditions that do not otherwise effect the peptide structure. The first amino acid is amino protected then coupled to the resin. Amino protecting groups include, but are not limited to, 9-fluorenyl-methyloxycarbonyl (FMOC) and t-butoxycarbonyl (BOC). The amino protecting group is then removed using conventional methods. After removal of the amino protecting group, the remaining amino-protected amino acids (side-chain protected, if necessary) are sequentially added to produce the desired peptide or peptidomimetic.

The phosphotyrosine mimic according to this invention may also be functional group protected, if desired, and added to the growing peptide chain as described above. Functional group protection is well within the ordinary skill of the art and is typically carried out as described above for side group protection. Other protecting groups useful for side chain or functional group protection according to this invention may be found in well-known organic chemistry references. It should also be appreciated that phosphotyrosine mimic-containing compounds according to this invention include the free form of such compounds as well as pharmaceutically acceptable salts of those compounds, where such forms exist.

The phosphotyrosine mimics according to this invention are structurally simple and advantageously, easily synthesized from commercially available starting materials using conventional synthetic techniques. Similarly, incorporation of a mimic into an appropriate molecular structure (and preferably, a peptide or peptidomimetic of a native tyrosine kinase-dependent regulatory protein ligand or receptor) is readily accomplished using known techniques and, preferably, the methodology detailed above.

It should be understood that only those compounds having combinations of variables that result in stable structures are included within the scope of this invention. Stable structures are those that can be produced according to the above mentioned techniques and stored for an acceptable period of time. Preferably, the stable structures are those that can be stored at 32° F. (0° C.) for at least one week without detectable levels of decomposition. In addition to the free forms of these compounds, this invention also includes the pharmaceutically acceptable salts thereof. The production of pharmaceutically acceptable salts of compounds according to this invention is well within the ordinary skill in the art.

Without wishing to be bound by theory, the phosphotyrosine mimics according to this invention, when incorporated into an appropriate molecular structure, are capable of binding tyrosine-kinase dependent regulatory proteins in a manner substantially similar or identical to that of the native phosphotyrosine-containing ligand. Therefore, the phosphotyrosine mimic-containing compounds are competitive inhibitors of that binding. Specifically, once bound, the phosphotyrosine mimics inhibit the ability of the regulatory protein to bind its native phosphotyrosine-containing receptor, thereby inhibiting cellular activation. It will be apparent from the nature of this discovery that the phosphotyrosine mimics according to this invention may be integrally used as antagonists to virtually any tyrosine kinase-dependent regulatory protein.

As antagonists of tyrosine kinase-dependent regulatory proteins, the phosphotyrosine mimic-containing structures according to this invention can be used to treat a variety of disorders, including those associated with or caused by neoplastic diseases or chronic inflammatory diseases. Specifically, by blocking or displacing the binding of the native phosphotyrosine-containing ligands or receptors of these regulatory proteins, the phosphotyrosine mimic-containing structures according to this invention effectively disrupt the associated regulatory cascades. Representative neoplastic diseases that are treatable with the phosphotyrosine mimic-containing antagonists according to this invention include (but are not limited to): leukemias (including, but not limited to, acute lymphocytic, acute lymphoblastic, chronic lymphocytic, acute myloblastic and chronic mylocytic), carcinomas (including, but not limited to, adenocarcinoma and that of the colon, ovaries, cervix, esophagus, stomach, small intestines, pancreas and lungs), sarcomas (including, but not limited to oesteroma, osteosarcoma, lepoma, liposarcoma, hemangioma, hemangiosarcoma and Karposi's sarcoma), malignant melanomas (including, but not limited to, amelanotic and melanotic), mixed types of neoplasias (such as, but not limited to, carcinosarcoma, lymphoid tissue type, folicullar reticulum, cell sarcoma and Hodgkin's disease), neuroblastoma, cerebral malaria, capillary leak syndrome, hematological malignancies and the like. Representative chronic inflammatory diseases treatable with the phosphotyrosine mimic-containing antagonists according to this invention include (but are not limited to): rheumatoid arthritis, multiple sclerosis. Guillain-Barre syndrome, Crohn's disease, ulcerative colitis, psoriasis, graft versus host disease, lupus erythematosus and insulin-dependent diabetes mellitus.

The present invention provides pharmaceutical compositions comprising a therapeutically effective amount of a phosphotyrosine mimic-containing substance according to this invention or, if desired, a pharmaceutically acceptable salt thereof. The compounds or pharmaceutical compositions according to this invention may be used to treat any of the disease states mentioned above by administering a therapeutically effective amount of a compound or composition according to this invention to a patient. For such treatment, the preferred phosphotyrosine mimic-containing substance is a peptide or peptidomimetic of a phosphotyrosine-containing ligand or receptor of a tyrosine-kinase dependent regulatory protein.

A therapeutically effective amount refers to an amount which is effective, upon single or multiple dose administration to the patient, in controlling the growth of a neoplasm, in alleviating, in whole or in part, the symptoms of the chronic inflammatory disorder, prolonging the survivability or improving the clinical disposition or physical well-being of the patient. Treatment according to this invention may or may not completely eradicate the symptoms or the disorder being treated. A therapeutically effective amount can be readily determined by the attending diagnostician by the use of known techniques and by observing the results obtained under analogous circumstances. In determining a therapeutically effective amount, a number of factors are considered by the attending diagnostician, including (but not limited to): the species of mammal; its size, age and general health; the specific disease involved; the degree of or involvement or the severity of the disease; the response of the individual patient; the particular compound or composition administered; the mode of administration; the bioavailability characteristics of the preparation administered; the dose regimen selected; the use of concomitant mediation and other relevant circumstances.

The compounds and pharmaceutical compositions according to this invention may be administered to the patient in any pharmaceutically acceptable and effective dosage form. Examples of such dosage forms include (but are not limited to): intravenous, intramuscular, subcutaneous, intra-articular, intrasynovial, intrathecal, periostal, intratumoral, peritumoral, intralesional, perilesional, infusion, sublingual, buccal, transdermal, oral, topical or inhalation. Preferred dosage forms include oral, topical, intravenous, subcutaneous and transdermal.

In general, a therapeutically effective amount of a compound according to this invention is expected to vary in the range of about 0.1 mg/kg body weight/day (mg/kg/day) to about 100 mg/kg/day. Preferred amounts should range from about 0.1 mg/kg/day to about 50 mg/kg/day. More specifically, preferred dosage levels for various modes of administration are: intravenous (from about 0.1 mg/kg/day to about 40 mg/kg/day); intramuscular (from about 1 mg/kg/day to about 50 mg/kg/day); orally (from about 5 mg/kg/day to about 100 mg/kg/day); intranasal instillation (from about 5 mg/kg/day to about 100 mg/kg/day); and aerosol (from about 5 mg/kg/day to about 100 mg/kg/day).

Dosage forms may include any pharmaceutically acceptable carriers and adjuvants that are known to those of ordinary skill in the art. These carriers and adjuvants include, for example, ion exchangers, alumina, aluminum stearate, lecithin, serum proteins (such as human serum albumin), buffer substances (such as phosphates), glycine, sorbic acid, potassium sorbate, partial glyceride mixtures of saturated vegetable fatty acids, water, salts or electrolytes (such as protamine sulfate, disodium hydrogen phosphate, potassium hydrogen phosphate or sodium chloride), zinc salts, colloidal silica, magnesium trisilicate, polyvinyl pyrrolidone, cellulose-based substances and glycols (such as polyethylene glycol). Such forms include (but are not limited to) tablet, capsule, caplet, liquid, solution, suspension, emulsion, lozenges, syrup, reconstitutable powder, granule, suppository and transdermal patch. Methods for preparing such dosage forms are well known (see, for example, H. C. Ansel and N. G. Popovish, *Pharmaceutical Dosage Forms and Drug Delivery Systems,* 5th edition, Lea and Febiger, 1990).

The compounds of this invention may be administered alone or in combination with one or more conventional anti-neoplastic or anti-inflammatory agent. Such agents are well known and may be selected as circumstances dictate by those of ordinary skill in the art. Advantageously, such combination therapy may utilize lower dosages of the conventional therapeutic agents, thereby avoiding possible toxicity and adverse side effects incurred when those agents are administered as monotherapies. For example, the compounds of this invention may be used in combination with conventional cancer drugs (such as methotrexate, taxol, 5-fluorouracil, cis-platinum, cortisone, nitrogen mustards, thiotepa and nitrosoureas) and conventional anti-inflammatory drugs (such as non-steroidal anti-inflammatory agents, penicillamine, methotrexate, cortisone and gold salts).

Besides their therapeutic utility, the phosphotyrosine mimics of this invention may also be used to identify, isolate and purify regulatory proteins or fragments thereof that possess native phosphotyrosine-containing ligands or receptors. For example, it is possible to covalently link the phosphotyrosine mimics according to this invention (or compounds comprising them) to a solid support material, thereby creating an affinity chromatography matrix. Cell preparations may be passed through such a matrix to identify new tyrosine-kinase dependent regulatory proteins or alternatively, to isolate and purify known proteins. In many cases, phosphotyrosine (or a compound containing a phosphotyrosine residue) cannot be used for this purpose, given phosphotyrosine's strong polarity and tendency to hydrolyze. It will be clear to those of ordinary skill in the art that the generality and multiple utilities of the methods described herein are unique and desirable features of this invention.

The following examples are provided to illustrate the invention described herein. These examples demonstrate various preferred embodiments of this invention and are not to be construed as limiting the scope of the invention in any way.

SYNTHESIS OF PHOSPHOTYROSINE MIMICS

The following describes synthetic schemes useful for producing representative phosphotyrosine mimic compounds of formula (I).

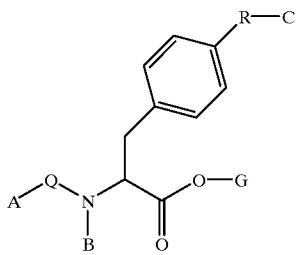

wherein:

A,B,C,G,Q and R are defined hereinabove. The synthesis of compounds according to the invention may be accomplished by methods similar to those described in the literature or known to those skilled in the art. Some of these methods are exemplified in the synthetic examples below, other may be found in related U.S. application Ser. No. 09/208,113, incorporated herein by reference in it's entirety.

2-(S)-$^t$Butoxycarbonylamino-3-[4'-(1"-$^t$butoxycarbonyl-1"-methyl)ethyl]benzenepropanoic acid Scheme 1

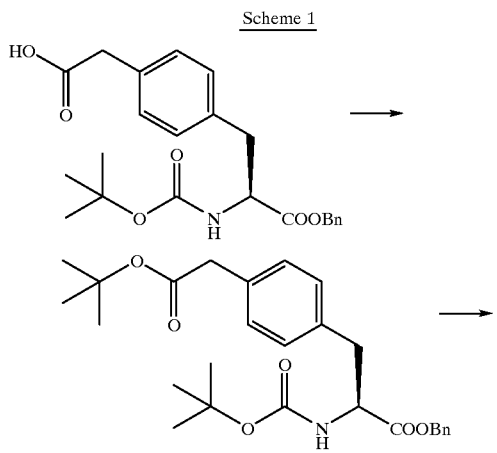

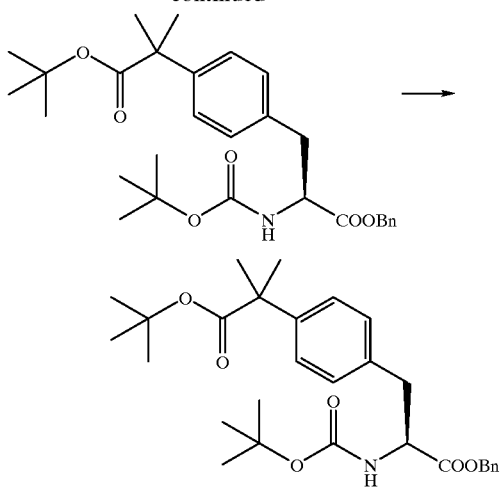

2-(S)-$^t$Butoxycarbonylamino-3-(4'-$^t$butoxycarbonylmethyl)benzenepropanoic acid benzyl ester A mixture of 2-(S)-$^t$butoxycarbonylamino-3-[(4'-carboxymethyl)benzene]propanoic acid benzyl ester (J. W. Tilley et al., *J. Org. Chem.*, 55, pp. 906–10 (1990)) (6.67 g, 16.2 mmol) and dimethylformamide di-$^t$butyl acetal (19.4 mL, 80.9 mmol) in toluene (120 mL) was heated at 85° C. for 2 hours under nitrogen. The mixture was diluted with ethyl acetate, washed with water, dried, filtered and evaporated. Chromatography of the residue over silica gel (15% ethyl acetate/hexane) gave 2-(S)-$^t$butoxycarbonylamino-3-(4'-$^t$butoxycarbonylmethyl)benzenepropanoic acid benzyl ester (3.77 g, 50%).

2-(S)-$^t$Butoxycarbonylamino-3-[4'-(1"-$^t$butoxycarbonyl-1"-methyl)ethyl]benzenepropanoic acid benzyl ester A cooled (–78° C.) solution of 2-(S)-$^t$butoxycarbonylamino-3-[4'-($^t$butoxycarbonylmethyl)benzene]propanoic acid benzyl ester (3.77 g, 8.06 mmol) in THF (20 mL) was cannulated, over 25 minutes, into a stirred solution of potassium bis(trimethylsilyl)amide (0.8 M in THF, 21.2 mL, 16.9 mmol) at –78° C. After 30 minutes at –78° C., iodomethane (0.75 mL, 12 mmol) was added. After 1 hour 45 minutes at –78° C., the mixture was poured into cold 10% citric acid (300 mL). The aqueous phase was extracted with ethyl acetate. The organic phase was washed with aqueous $Na_2S_2O_3$, saturated $NaHCO_3$, and brine, dried ($MgSO_4$), filtered and concentrated. The residue was subjected twice more to the same alkylation conditions to introduce the second methyl group. Chromatography over silica gel gave 2-(S)-$^t$butoxycarbonylamino-3-[4'-(1"-$^t$butoxycarbonyl-1"-methyl)ethyl]benzenepropanoic acid benzyl ester (3.36 g, 6.78 mmol, 84%).

2-(S)-$^t$Butoxycarbonylamino-3-[4'-(1"-$^t$butoxycarbonyl-1"-methyl)ethyl]benzenepropanoic acid A mixture of 2-(S)-$^t$butoxycarbonylamino-3-[4'-(1"-$^t$butoxyoxycarbonyl-1"-methyl)ethyl]benzenepropanoic acid benzyl ester (3.92 g, 7.91 mmol), 10% Pd/C (1.25 g) and cyclohexene (8.01 mL, 79 mmol) in ethanol (125 mL) was heated at 70–75° C. for 15 minutes. The mixture was cooled and filtered. Evaporation of the solvents gave 2-(S)-*t*butoxycarbonylamino-3-[4'-(1"-*t*butoxycarbonyl-1"-methyl)ethyl]benzenepropanoic acid (3.20 g, 99%).

2-(S)-*t*Butoxycarbonylamino-3-[4'-(1"-benzyloxycarbonyl-1"-methyl)ethyl]benzenepropanoic acid

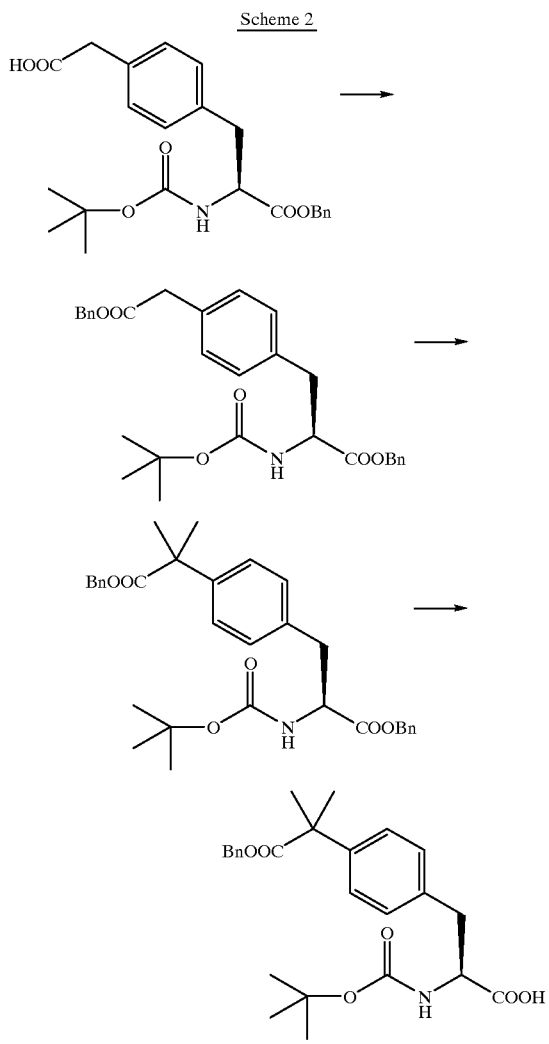

2-(S)-*t*Butoxycarbonylamino-3-(4'-benzyloxycarbonylmethyl)benzenepropanoic acid benzyl ester To a stirred solution of 2-(S)-*t*butoxycarbonylamino-3-(4'-carboxymethyl)benzene]propanoic acid benzyl ester (7.6 g, 18.4 mmol) in acetonitrile (150 mL), cooled to 0° C., under nitrogen was added DBU (3.03 mL, 20.3 mmol) and benzyl bromide (2.41 mL, 20.3 mmol). The cooling bath was removed and the mixture was stirred at rt for 5 hours. Aqueous ammonium chloride was added, and the mixture was extracted with ethyl acetate. The organic phase was dried, filtered and evaporated. Chromatography of the residue over silica gel (10% to 20% ethyl acetate/hexane) gave 2-(S)-*t*butoxycarbonylamino-3-(4'-benzyloxycarbonylmethyl)benzenepropanoic acid benzyl ester (9.7 g, 100%).

2-(S)-*t*Butoxycarbonylamino-3-[4'-(1"-benzyloxycarbonyl-1"-methyl)ethyl]benzenepropanoic acid benzyl ester A cold (−78° C.) solution of 2-(S)-*t*butoxycarbonylamino-3-[4'-(benzyloxycarbonylmethyl)benzene]propanoic acid benzyl ester (7.20 g, 14.3 mmol) in THF (48 mL) was slowly cannulated into a stirred solution of potassium bis(trimethylsilyl)amide (0.8M in THF, 37.5 mL, 30.0 mmol) at −78° C. After 30 minutes at −78° C., iodomethane (1.3 mL, 21 mmol) was added. After 1 hour 45 minutes at −78° C., the mixture was poured into cold 10% citric acid (300 mL). The aqueous phase was extracted with ethyl acetate and the organic phase was washed with 10% $Na_2S_2O_3$, saturated $NaHCO_3$, water and brine. The organic phase was dried ($MgSO_4$), filtered, and concentrated. The residue was subjected to the same reaction conditions in order to introduce the second methyl group. Chromatography over silica gel (10% to 15% ethyl acetate/hexane) gave 2-(S)-*t*butoxycarbonylamino-3-[4'-(1"-benzyloxycarbonyl-1"-methyl)ethyl]benzenepropanoic acid benzyl ester (6.10 g, 11.5 mmol, 80%).

2-(S)-*t*Butoxycarbonylamino-3-[4'-(1"-benzyloxycarbonyl-1"-methyl)ethyl]benzenepropanoic acid To a stirred solution of 2-(S)-*t*butoxycarbonylamino-3-[4'-(1"-benzyloxycarbonyl-1"-methyl)ethyl]benzenepropanoic acid benzyl ester (5.39 g, 10.2 mmol) in methanol (125 mL) and THF (230 mL) at 0° C. was added a cold solution of lithium hydroxide (0.86 g, 20.4 mmol) in water (125 mL). After 2.5 hours at 0° C., the mixture was diluted with water (250 mL), and washed 3 times with ether. The aqueous phase was acidified with 10% citric acid, and extracted with ethyl acetate. The combined organic phase was washed with water and brine, dried ($Na_2SO_4$), filtered, and concentrated to give 2-(S)-*t*butoxycarbonylamino-3-[4'-(1"-benzyloxycarbonyl-1"-methyl)ethyl]benzenepropanoic acid (4.13 g, 9.36 mmol, 92%).

2-(S)-*t*Butoxycarbonylamino-3-[4'-(1"-trimethylsilylethyloxycarbonyl-1"-methyl)ethyl]benzenepropanoic acid

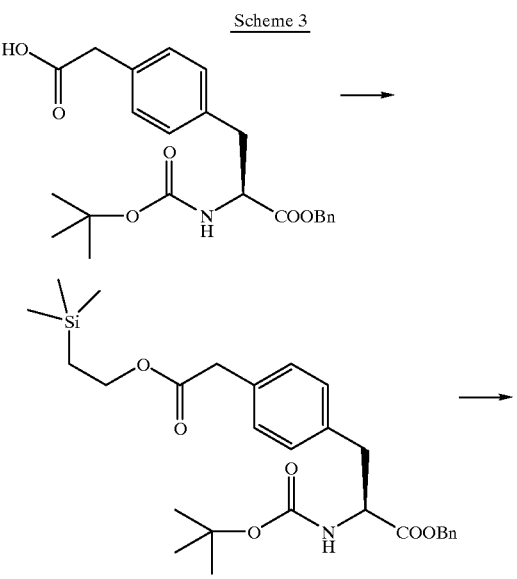

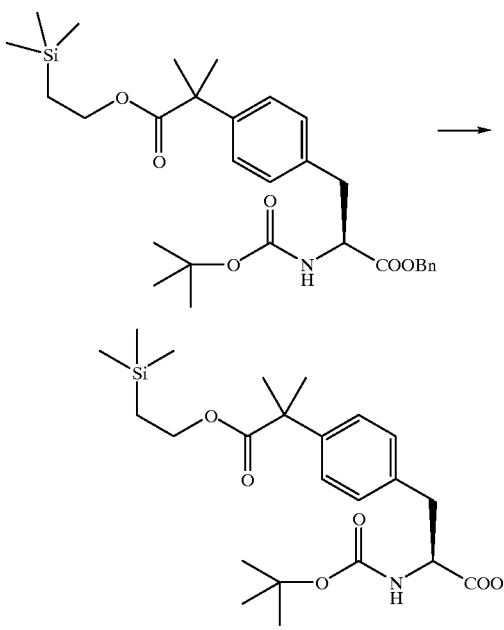

2-(S)-'Butoxycarbonylamino-3-(4'-trimethylsilylethyloxycarbonylmethyl)benzenepropanoic acid benzyl ester To a stirred suspension of 2-chloro-1-methylpyridinium iodide (2.02 g, 7.89 mmol) in methylene chloride (3 mL,) was added 2-(S)-'butoxycarbonylamino-3-(4'-carboxymethyl)benzenepropanoic acid benzyl ester (2.17 g, 5.26 mmol), 2-trimethylsilylethanol (1.13 mL, 7.89 mmol), and triethylamine (2.27 mL, 16.3 mmol) in methylene chloride (12 mL). After 10 hours, water and ethyl acetate were added, and the organic phase was washed with water and brine, dried (MgSO$_4$), filtered, and evaporated. Chromatography of the residue over silica gel (5% ethyl acetate/hexane) gave 2-(S)-'butoxycarbonylamino-3-(4'-trimethylsilylethyloxycarbonylmethyl)benzenepropanoic acid benzyl ester (2.72 g, 100%).

2-(S)-'Butoxycarbonylamino-3-[4'-(1"-trimethylsilylethyloxycarbonyl-1"-methyl)ethyl]benzenepropanoic benzyl ester To a stirred solution of 2-(S)-'butoxycarbonylamino-3-(4'-trimethylsilylethyloxycarbonylmethyl)benzenepropanoic acid benzyl ester (4.29 g, 8.8 mmol) in THF (40 mL), cooled to –78° C., was added a solution of lithium bis(trimethylsilyl)amide (1M in THF, 19.2 mL, 19 mmol). After 45 minutes, iodomethane (1.04 mL, 18 mmol) was added and stirring was continued for an additional 1.5 hours. Acetic acid (5 mL) was added, and the mixture was allowed to warm to rt. Ether (500 mL) was added, and the organic phase was washed with 10% citric acid, 10% NaHCO$_3$, 1M NaOH, and brine, dried (MgSO$_4$), and concentrated. The residue was subjected to the same reaction conditions but using potassium bis(trimethylsilyl)amide as the base in order to introduce the second methyl group. 2-(S)-'Butoxycarbonylamino-3-[4'-(1"-trimethylsilylethyloxycarbonyl-1"-methyl)ethyl]benzenepropanoic benzyl ester was obtained as a yellow oil (2.0 g, 69%).

2-(S)-'Butoxycarbonylamino-3-[4'-(1"-trimethylsilylethyloxycarbonyl-1"-methyl)ethyl]benzenepropanoic acid A mixture of 2-(S)-'butoxycarbonylamino-3-[4'-(1"-trimethylsilylethyloxycarbonyl-1"-methyl)ethyl] benzenepropanoic benzyl ester (0.823 g, 1.52 mmol) and 10% Pd/C (0.082 g) in ethanol (10 mL) was hydrogenated at 1 atmosphere for 1 hour. The catalyst was removed by filtration, and the solvent was evaporated to give 2-(S)-'butoxycarbonylamino-3-[4'-(1"-trimethylsilylethyloxycarbonyl-1"-methyl)ethyl]benzenepropanoic acid as a colorless oil (0.65 g, 96%).

2-(S)-'Butoxycarbonylamino-3-[4'-(1"-(R,S)-trimethylsilylethyloxycarbonyl)ethyl]benzenepropanoic acid Scheme 4

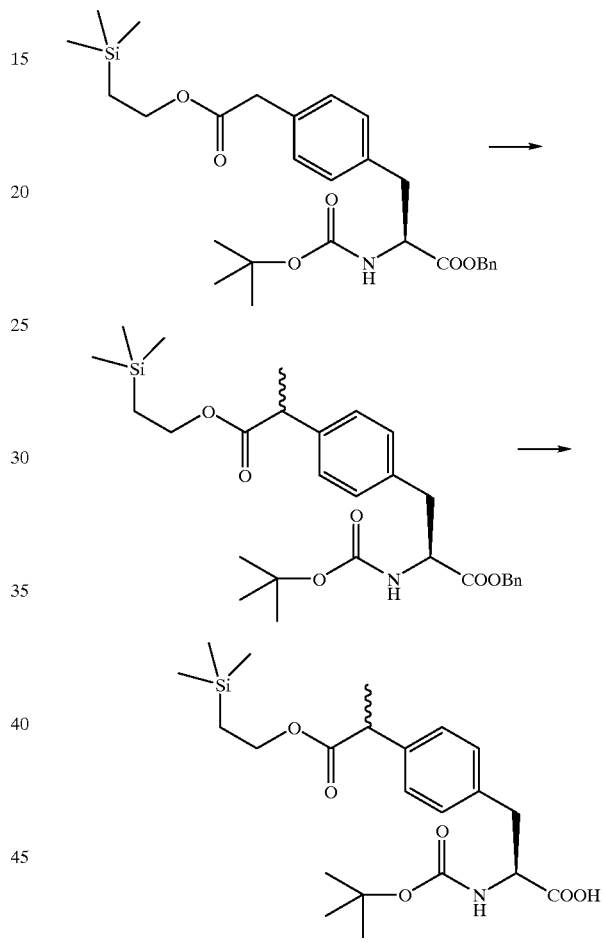

2-(S)-'Butoxycarbonylamino-3-[4'-(1"-(R,S)-trimethylsilylethyloxycarbonyl)ethyl]benzenepropanoic acid benzyl ester To a stirred solution of 2-(S)-'butoxycarbonylamino-3-(4'-trimethylsilylethyloxycarbonylmethyl)benzenepropanoic acid benzyl ester (4.29 g, 8.8 mmol) in THF (40 mL) cooled to –78° C. was added a solution of lithium bis(trimethylsilyl)amide (1M in THF, 19.2 mL, 19.2 mmol). After 45 minutes, iodomethane (1.04 mL, 18 mmol) was added, and stirring was continued for 1.5 hours. Acetic acid (5 mL) was added, the mixture warmed to rt, and ether (500 mL) was added. The solution was washed with 10% citric acid, 10% NaHCO$_3$, 1M NaOH and brine. The organic phase was dried (MgSO$_4$), and concentrated to give 2-(S)-'butoxycarbonylamino-3-[4'-(1"-(R,S)-trimethylsilylethyloxycarbonyl)ethyl]benzenepropanoic acid benzyl ester (4.35 g, 98%).

Conversion to 2-(S)-'butoxycarbonylamino-3-[4'-(1"-(R,S)- trimethylsilylethyloxycarbonyl)ethyl]benzenepropanoic acid was carried out in the same manner as described above for the deprotection of 2-(S)-'butoxycarbonylamino-3-[4'-(1"-trimethylsilylethyloxycarbonyl-1"-methyl)ethyl] benzenepropanoic benzyl ester.

2-(R,S)-Benzyloxycarbonylamino-3-[4'-(1"-'butoxycarbonyl-1"-methyl)ethyl]benzenepropanoic acid

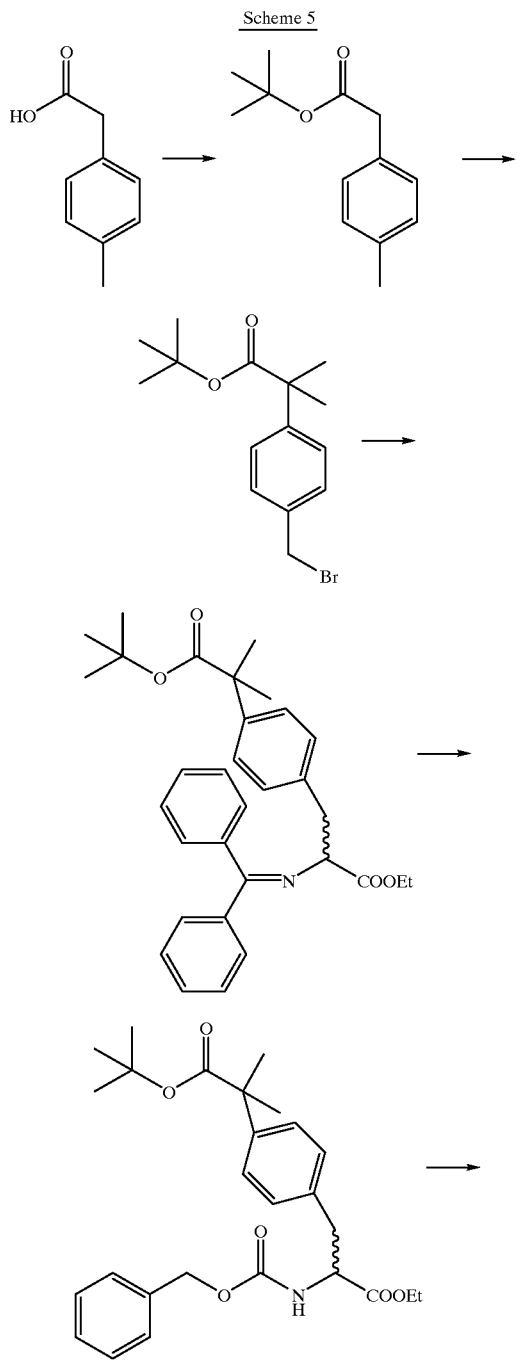

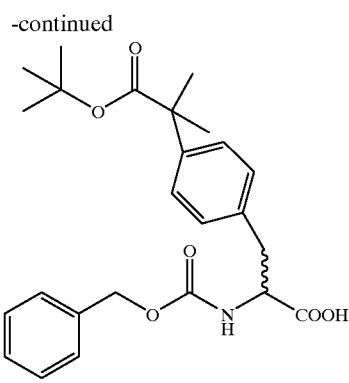

'Butyl 4-methylphenylacetate

To a stirred solution of 4-methylphenylacetic acid (20.6 g, 137 mmol) in methylene chloride (100 mL) in a pressure flask cooled on a dry-acetone bath was added isobutene (190 mL) followed by concentrated sulfuric acid (2.5 mL). After 36 hours, the mixture was cooled (dry ice/acetone bath) and isobutene was removed in a slow stream of nitrogen. The residue was treated with 10% $NaHCO_3$, and extracted with methylene chloride (3×100 mL). The combined methylene chloride extract was washed with 10% $NaHCO_3$ and brine, and dried ($Na_2SO_4$). Evaporation of the solvent gave 'butyl 4-methylphenylacetate as a colorless oil (25 g, 90%).

'Butyl 2-(4-methylphenyl)-2,2-dimethylacetate

To a stirred solution of potassium 'butoxide (1M in THF, 100 mL) under argon in THF (150 mL) cooled to 0° C. was added 'butyl 4-methylphenylacetate (19.3 g, 93.5 mmol) in THF (50 mL). After 30 minutes, iodomethane (7 mL) in THF (10 mL) was added over 15 minutes and the mixture was stirred for 45 min. Additional potassium 'butoxide (1M in THF, 120 mL) was added followed, after 1 hour, by iodomethane (8 mL) in THF (25 ml). The mixture was allowed to warm to rt overnight, and the solvent was evaporated. The residue was taken up in 1N sulfuric acid (250 mL), and extracted with ether (3×100 mL). The combined organic phase was washed with brine, dried ($Na_2SO_4$), and evaporated to give 'butyl 2-(4-methylphenyl)-2,2-dimethylacetate as a light yellow oil (19.4 g, 83 mmol, 89%).

'Butyl 2-(4-bromomethylphenyl)-2,2-dimethylacetate

To a solution of 'butyl 2-(4-methylphenyl)-2,2-dimethylacetate (19.4 g, 83 mmol) in carbon tetrachloride (350 mL) was added N-bromosuccinimide (16.2 g, 92 mmol) and benzoyl peroxide (0.5 g). The mixture was heated under reflux for 1 hour. The mixture was cooled to rt, and the precipitate was removed by filtration. The filtrate was washed with 10% $NaHCO_3$ and brine, dried ($Na_2SO_4$), and evaporated to give 'butyl 2-(4-bromomethylphenyl)-2,2-dimethylacetate as a light yellow oil (26.4 g, 100%).

2-(R,S)-Benzyloxycarbonylamino-3-[4'-(1"-'butoxycarbonyl-1"-methyl)ethyl]benzenepropanoic acid ethyl ester To a stirred solution of 'butyl 2-(4-bromomethylphenyl)-2,2-dimethylacetate (6.3 g, 20 mmol) in THF (60 mL) cooled on ice was added N-(diphenylmethylene)glycine ethyl ester (5.6 g, 21 mmol). After 10 minutes, sodium bis(trimethylsilyl)amide (2M in THF, 11 mL) was added all at once. The mixture was stirred at 0° C. for 1 hour. The precipitated solid was removed, and the solvent was evaporated. The residue was taken up in acetic acid (20 mL), water (20 mL) and methanol (40 mL), and stirred at rt for 3 hours. The methanol was evaporated, and the aqueous phase was washed with 1/1 hexane/ether (2×50 mL). The combined organic phase was extracted with water (2×25 mL), and the combined aqueous phase was cooled on ice. The pH was adjusted to approximately pH 7 with sodium carbonate. Dioxane (60 ml,) was added followed by benzyl chloroformate (3.6 mL, 25 mmol). The mixture was stirred on ice for 1 hour, diluted with water (100 mL), acidified to pH 3 with 1N sulfuric acid, and extracted with ethyl acetate (3×100 mL). The combined ethyl acetate extract was washed with brine, dried ($Na_2SO_4$), and evaporated to give crude 2-(R,S)-benzyloxycarbonylamino-3-[4'-(1"-'butoxycarbonyl-1"-methyl)ethyl]benzenepropanoic acid ethyl ester as a light yellow oil (9.4 g).

This reaction was repeated with 20 g (63.6 mmol) of 'butyl 2-(4'-bromomethylphenyl)-2,2-dimethylacetate to give additional 2-(R,S)-benzyloxycarbonylamino-[4'-(1"-'butoxycarbonyl-1"-methyl)ethyl]benzenepropanoic acid ethyl ester (30 g). The two batches were combined and purified by chromatography over silica gel (hexane/ethyl acetate 9/1) to give 2-(R,S)-benzyloxycarbonylamino-3-[4'-(1"-'butoxycarbonyl-1"-methyl)ethyl]benzenepropanoic acid ethyl ester as a colorless oil (23.7 g, 50.6 mmol, 54% from 'butyl 2-(4-bromomethyl)phenyl-2,2-dimethylacetate).

2-(R,S)-Benzyloxycarbonylamino-3-[4'-(1"-'butoxycarbonyl-1"-methyl)ethyl]benzenepropanoic acid was obtained by lithium hydroxide hydrolysis of 2-(R,S)-benzyloxycarbonylamino-[4'-(1"-'butoxycarbonyl-1"-methyl)ethyl]benzenepropanoic acid ethyl ester by a procedure similar to that described above in the synthesis of 2-(R,S)-benzyloxycarbonylamino-3-[4'-(1"-'butoxycarbonyl)cyclopentyl]benzenepropanoic acid.

2-(S)-'Butoxycarbonylamino-3-[4'-(1"-'butoxycarbonyl)cyclopropyl]benzenepropanoic acid 2-(R,S)-'Butoxycarbonylamino-3-[4'-(1"-'butoxycarbonyl-1"-methyl)ethyl]benzenepropanoic acid Scheme 6

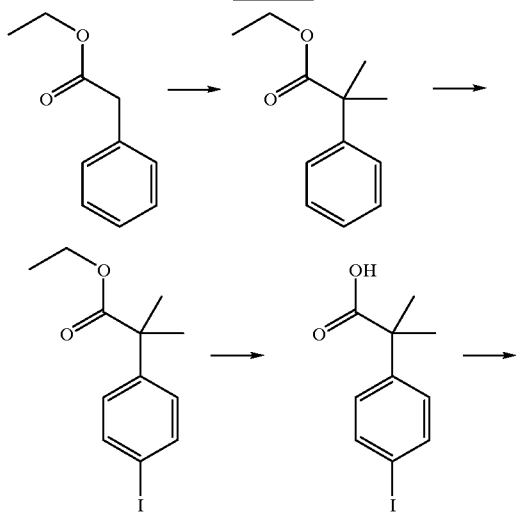

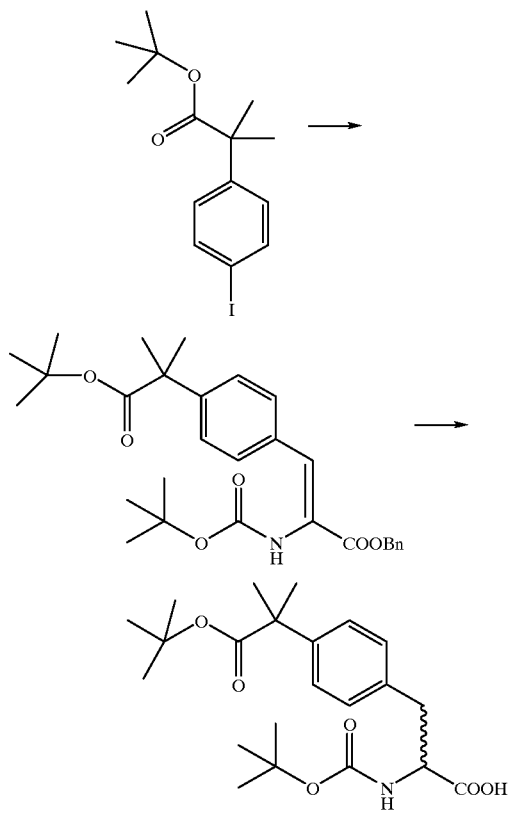

(1'-Ethoxycarbonyl-1'-methyl)ethylbenzene

To a solution of ethyl phenylacetate (32.8 g, 200 mmol) in THF (1000 mL) under argon was added sodium bistrimethylsilylamide (2M in THF, 100 mL). After 45 minutes. methyl iodide (13 mL) was added over 15 minutes and the mixture was stirred at rt for 30 minutes. Additional sodium bistrimethylsilylamide (2M in THF, 100 mL) was added, followed, after 30 minutes, by methyl iodide (14 mL). After 30 minutes the mixture was diluted with hexane and washed with water. The organic phase was dried, filtered and evaporated to give (1'-ethoxycarbonyl-1'-methyl)ethylbenzene (28.0 g, 146 mmol, 73%).

4-Iodo-(1'-carboxy-1'-methyl)ethylbenzene

A mixture of (1'-ethoxycarbonyl-1'-methyl)ethylbenzene (28.0 g, 146 mmol), iodine (24.7 g). sodium iodate (7.1 g) and concentrated sulfuric acid (4 mL) in acetic acid (200 mL,) was stirred and heated at 55° C. for 90 hours. The solvent was evaporated and the residue was partitioned between water and hexane. The organic phase was washed with aqueous sodium thiosulfate, dried, filtered, and evaporated. The residue was taken up in ethanol (200 mL) and water (100 mL), and potassium hydroxide (20 g) was added. The mixture was heated under reflux for 5 hours, and cooled to rt. The mixture was washed with hexane. The aqueous phase was acidified with concentrated hydrochloric acid, and extracted with hexane. The organic phase was dried, filtered and evaporated to give 4-iodo-(1'-carboxy-1'-methyl)ethylbenzene as a solid (19.6 g, 67 mmol, 46%).

4-Iodo-(1'-'butoxycarbonyl-1'-methyl)ethylbenzene

To a solution of 4-iodo-(1'-carboxy-1'-methyl)ethylbenzene (18.7 g, 64.3 mmol) in methylene chloride (150 mL) was added dimethylformamide (0.5 mL) followed by oxalyl chloride (10 mL) dropwise. After 1 hour the solvent was evaporated and the residue was taken up in THF (100 ml,), and cooled on ice. Potassium ᵗbutoxide (1M in THF, 75 mL) was added over 20 minutes. The mixture was diluted with hexane, washed with water, dried, filtered and evaporated. The residue was triturated with methanol/water to give 4-iodo-(1'-ᵗbutoxycarbonyl-1'-methyl)ethylbenzene as a solid (18.1 g, 52.1 mmol, 81%).

2-ᵗButoxycarbonylamino-3-[4'-(1"-ᵗbutoxycarbonyl-1"-methyl)ethyl]benzenepropenoic acid, benzyl ester A mixture of benzyl (2-ᵗbutoxycarbonylamino)acrylate (8.00 g, 27.9 mmol), 4-iodo-(1'-ᵗbutoxycarbonyl-1'-methyl) ethylbenzene (7.03 g, 20.3 mmol), sodium bicarbonate (4.03 g), tetrabutylammonium chloride hydrate (6.47 g) and palladium acetate (0.41 g) in dimethylformamide (100 mL) was degassed and covered with argon three times. The mixture was heated under argon at 80° C. for 5 hours. The mixture was cooled, diluted with ethyl acetate/hexane and washed with water. The organic phase was dried, filtered and evaporated. Chromatography of the residue over silica gel (ethyl acetate/hexane 98/2 to 9/1) gave 2-ᵗbutoxycarbonylamino-3-[4'-(1"-ᵗbutoxycarbonyl-1"-methyl)ethyl] benzenepropenoic acid, benzyl ester as an oil that solidified upon trituration with hexane (7.24 g, 14.6 mmol, 72%).

2-(R,S)-ᵗButoxycarbonylamino-3-[4'-(1"-ᵗbutoxycarbonyl-1"-methyl)ethyl]benzenepropanoic acid A mixture of 2-ᵗbutoxycarbonylamino-3-[4'-(1"-ᵗbutoxycarbonyl-1"-methyl)ethyl]benzenepropenoic acid, benzyl ester (7.39 g, 14.9 mmol) and 10% Pd/C (0.202 g) in ethanol (75 mL) was hydrogenated at 45 psi in a Parr apparatus for 26 hours. The catalyst was removed by filtration and the solvent was evaporated. The residue crystallized from hexane giving 2-(R,S)-ᵗbutoxycarbonylamino-3-[4'-(1"-ᵗbutoxycarbonyl-1"-methyl)ethyl]benzenepropanoic acid (4.67 g, 11.5 mmol, 77%).

2-(S)-ᵗButoxycarbonylamino-3-[4'-(1"-hydroxy-1"-methoxycarbonyl)methyl]benzenepropanoic acid Scheme 7

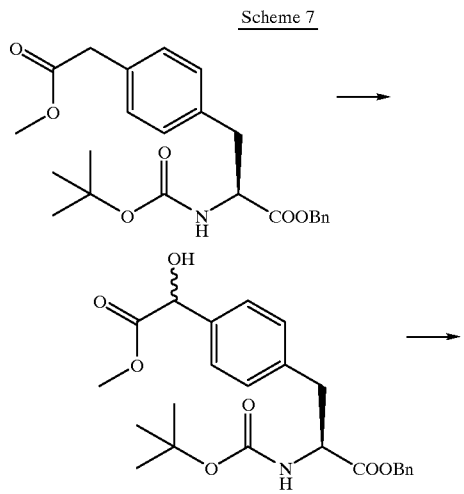

2-(S)-ᵗButoxycarbonylamino-3-[4'-(1"-hydroxy-1"-methoxycarbonyl)methyl]benzenepropanoic acid benzyl ester To a stirred solution of 2-(S)-ᵗbutoxycarbonylamino-3-(4'-methoxycarbonylmethyl)benzenepropanoic acid benzyl ester (1.28 g, 3.0 mmol) in dry THF (15 mL) cooled to −78° C. under argon was added a cooled (−78° C.) solution of potassium bis(trimethylsilyl)amide (0.81M in THF, 9.3 mL, 7.5 mmol). After 45 minutes, N-phenylsulfonylphenyloxaziridine (1.18 g, 4.5 mmol) in THF (15 mL) cooled to −78° C. was added, and the mixture was stirred for 40 minutes at −78° C. The reaction was quenched with saturated NH₄Cl (10 mL), and the mixture was extracted with ether and ethyl acetate. The combined extract was washed with saturated NH₄Cl, 5% NaHCO₃, 0.5N HCl and brine, dried (MgSO₄), and evaporated. Chromatography of the residue over silica gel (hexane/ethyl acetate 4/1) gave 2-(S)-ᵗbutoxycarbonylamino-3-[4'-(1"-hydroxy-1"-methoxycarbonyl)methyl]benzenepropanoic acid benzyl ester (1.02 g, 77%).

2-(S)-ᵗButoxycarbonylamino-3-[4'-(1"-hydroxy-1"-methoxycarbonyl)methyl]benzenepropanoic acid A mixture of 2-(S)-ᵗbutoxycarbonylamino-3-[4'-(1"-hydroxy-1"-methoxycarbonyl)methyl]benzenepropanoic acid benzyl ester (0.330 g, 0.744 mmol) and 5% Pd/C (0.050 g) in ethanol (10 mL) was hydrogenated at 1 atmosphere for 30 minutes. The catalyst was removed by filtration, and the solvent was evaporated to give 2-(S)-ᵗbutoxycarbonylamino-[4'-(1"-hydroxy-1"-methoxycarbonyl)methyl]benzenepropanoic acid.

2-(S)-ᵗButoxycarbonylamino-3-[4'-(1"-ᵗbutoxycarbonyl)cyclopropyl]benzenepropanoic acid Scheme 8

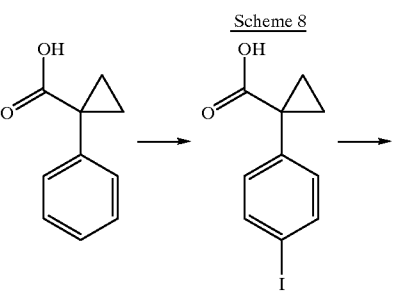

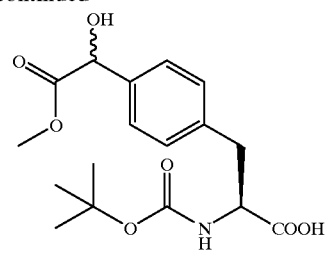

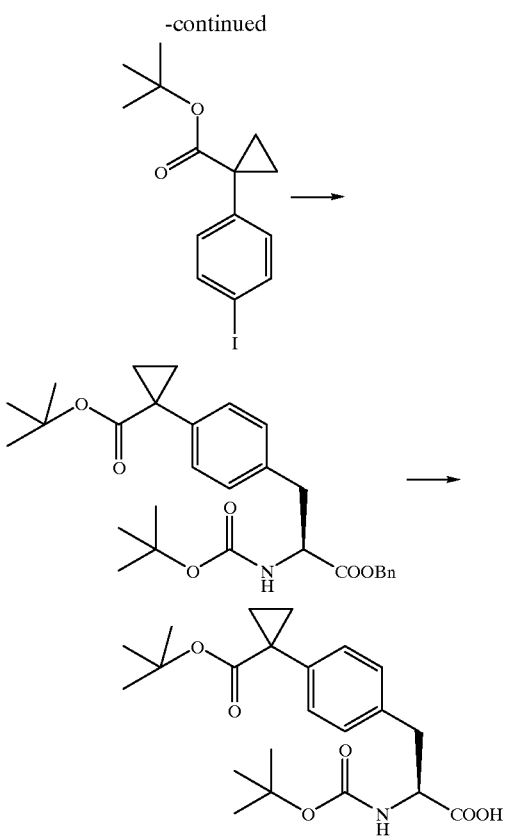

1-(4-Iodophenyl)cyclopropane-1-carboxylic acid

A mixture of 1-phenylcyclopropane carboxylic acid (16.5 g, 101 mmol), sodium iodate (5.04 g) and concentrated sulfuric acid (1 mL) in acetic acid (70 mL) was stirred and heated at 70° C. for 2 days. Additional sodium iodate (1.88 g) and sulfuric acid (1 mL) were added, and stirring was continued for 1 day. The acetic acid was evaporated, and the residue was partitioned between ethyl acetate and water. The organic phase was washed with aqueous sodium thiosulfate, dried, filtered, and evaporated. The solid residue was recrystallized form methanol/water to give 1-(4-iodophenyl) cyclopropane-1-carboxylic acid (7.98 g, 27 mmol, 27%).

$^t$Butyl 1-(4-iodophenyl)cyclopropane-1-carboxylate

To a solution of 1-(4-iodophenyl)cyclopropane-1-carboxylic acid (7.98 g, 27 mmol) in methylene chloride (200 mL) containing DMF (0.25 mL) was added dropwise over 30 minutes oxalyl chloride (3.2 mL). The mixture was stirred for 1 hour, and the solvent was removed under reduced pressure. The residue was taken up in THF (100 mL), and potassium $^t$butoxide (1M in THF, 35 mL) was added. After 30 minutes, the mixture was diluted with hexane, washed with water, dried, filtered and evaporated. The solid residue was recrystallized from methanol to give $^t$butyl 1-(4-iodophenyl)cyclopropane-1-carboxylate (5.74 g, 16.6 mmol, 62%).

2-(S)-$^t$Butoxycarbonylamino-3-[4'-(1"-$^t$butoxycarbonyl)cyclopropyl]benzenepropanoic acid benzyl ester A suspension of zinc (0.874 g) in THF with dibromoethane (0.02 mL) was sonicated at 40° C. for 40 minutes under argon. N-Boc-iodo-L-alanine benzyl ester (4.20 g, 10.4 mmol) and dimethylacetamide (5 mL) were added, and the mixture was heated at 55° C. for 1 hour. $^t$Butyl 1-(4-iodophenyl)cyclopropane-1-carboxylate (3.26 g, 9.48 mmol) in dimethylacetamide (10 ml,) was added followed by tris(dibenzylideneacetone)dipalladium(0) (0.33 g) and tri-o-tolylphosphine (0.398 g). Heating was continued under argon for 16 hours. The mixture was diluted with ethyl acetate, washed with water, dried, filtered and evaporated. Chromatography of the residue over silica gel (methylene chloride/hexane 1/3 to methylene chloride/ethyl acetate 95/5) gave 2-(S)-$^t$butoxycarbonylamino-3-[4'-(1"-$^t$butoxycarbonyl)cyclopropyl]benzenepropanoic acid benzyl ester (3.15 g, 6.36 mmol, 67%).

2-(S)-$^t$Butoxycarbonylamino-3-[4'-(1"-$^t$butoxycarbonyl)cyclopropyl]benzenepropanoic acid A mixture of 2-(S)-$^t$butoxycarbonylamino-3-[4'-(1"-$^t$butoxycarbonyl)cyclopropyl)benzene]propanoic acid benzyl ester (3.92 g, 7.92 mmol) and lithium hydroxide hydrate (0.60 g) in THF (10 mL) and water (5 mL) was stirred at rt for 16 hours. The mixture was acidified with potassium bisulfate (2N), and partitioned between ethyl acetate and water. The organic phase was separated, dried, filtered and evaporated. Chromatography of the residue over silica gel (methylene chloride/hexane to methylene chloride/ethyl acetate) gave 2-(S)-$^t$butoxycarbonylamino-3-[4'-(1"-$^t$butoxycarbonyl)cyclopropyl]benzenepropanoic acid (2.13 g, 5.25 mmol, 66%) as an oil that crystallized on standing.

2-(R,S)-Benzyloxycarbonylamino-3-[4'-(1"-$^t$butoxycarbonyl)cyclopentyl]benzenepropanoic acid Scheme 9

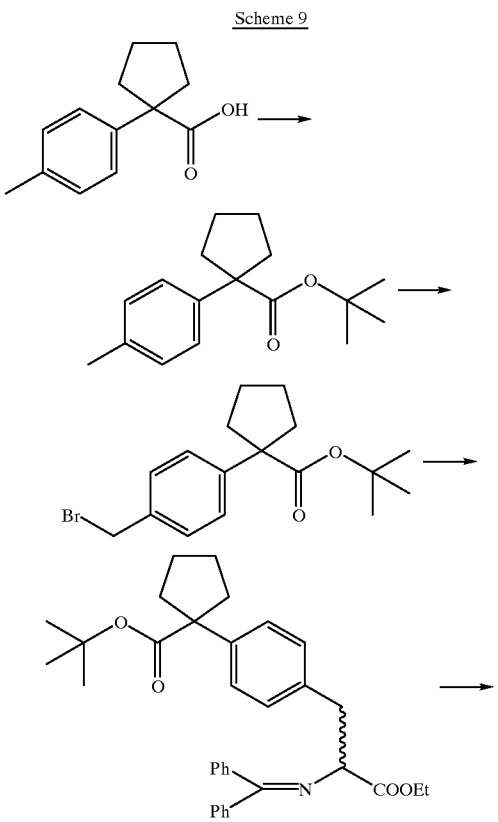

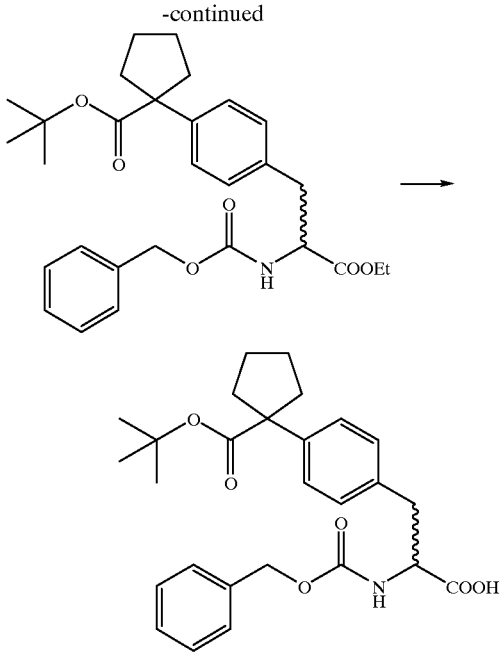

1-(4-Methylphenyl)cyclopentane carboxylic acid ᵗbutyl ester

To a suspension of 1-(4-methylphenyl)cyclopentane carboxylic acid (3.00 g, 14.7 mmol) in dichloromethane (50 ml,) at 0° C. was added oxalyl chloride (1.54 mL, 17.4 mmol) and DMF (2 drops). The mixture was stirred at 0° C. for 1 hour, and at rt for 2 hours. The solution was concentrated, diluted with THF (40 mL), and cooled to 0° C. Potassium ᵗbutoxide (1.80 g, 16.2 mmol) in THF (20 mL) was slowly added, and the mixture was stirred overnight at rt. Additional potassium ᵗbutoxide (0.660 g, 5.88 mmol) was added. After 20 minutes the solution was concentrated to dryness, and taken up in ethyl acetate. The organic phase was washed with 10% citric acid, saturated NaHCO₃ and brine, dried (MgSO₄), and concentrated. Flash column chromatography (10% ethyl acetate/hexane) gave 1-(4-methylphenyl)cyclopentane carboxylic acid ᵗbutyl ester (3.27 g, 87%).

1-(4-Bromomethylphenyl)cyclopentane carboxylic acid ᵗbutyl ester

To a solution of 1-(4-methylphenyl)cyclopentane carboxylic acid ᵗbutyl ester (2.00 g, 7.68 mmol) in CCl₄ (80 mL) was added N-bromosuccinimide (1.37 g, 7.68 mmol) and benzoyl peroxide (0.050 g). This mixture was brought to reflux by heating, and maintained at reflux for 2 hours using a sun lamp (250 W). Additional N-bromosuccinimide (0.34 g, 1.9 mmol) was added, and after 20 minutes the solution was concentrated to 40 mL. The white precipitate was removed by filtration. The filtrate was concentrated to give 1-(4-bromomethylphenyl)cyclopentane carboxylic acid ᵗbutyl ester (2.9 g, 100%) as a yellow oil which was used without additional purification.

2-(R,S)-Benzyloxycarbonylamino-3-[4'-(1"-ᵗbutoxycarbonyl)cyclopentyl]benzenepropanoic acid ethyl ester To a stirred solution of 1-(4-bromomethylphenyl)cyclopentane carboxylic acid ᵗbutyl ester (1.00 g, 2.95 mmol) and N-(diphenylmethylene)glycine ethyl ester (0.788 g, 2.95 mmol) in THF (12 mL) at 0° C. was added, over 10 minutes, sodium bis(trimethylsilyl)amide (1M in THF, 3.54 mL, 3.54 mmol). After 40 minutes, the mixture was filtered and concentrated. The residue was dissolved in ethyl acetate, washed with 10% citric acid, saturated NaHCO₃ and brine, and dried (MgSO₄).

Evaporation of the solvent gave 2-(R,S)-diphenylmethyleneamino-3-[4'-(1"-ᵗbutoxycarbonyl)cyclopentyl]benzenepropanoic acid ethyl ester which was hydrolysed by stirring in methanol (6 mL), water (3 mL) and acetic acid (3 mL) for 2 hours. The mixture was basified with sodium carbonate, and benzyl chloroformate (0.422 mL, 2.95 mmol) was added. After 1 hour, water and ethyl acetate were added. The organic phase was washed with 10% citric acid, saturated NaHCO₃ and brine, dried (MgSO₄), and concentrated. Flash chromatography (20% ethyl acetate/hexane) gave 2-(R,S)-benzyloxycarbonylaminmo-3-[4'-(1"-ᵗbutoxycarbonyl)cyclopentyl]benzenepropanoic acid ethyl ester (0.475 g, 0.958 mmol, 32% from 1-(4-bromomethylphenyl)cyclopentane carboxylic acid ᵗbutyl ester).

2-(R,S)-Benzyloxycarbonylamino-3-[4'-(1"-ᵗbutoxycarbonyl)cyclopentyl]benzenepropanoic acid A mixture of 2-(R,S)-benzyloxycarbonylamino-3-[4'-(1"-ᵗbutoxycarbonyl)cyclopentyl]benzenepropanoic acid ethyl ester (0.475 g, 0.96 mmol) and aqueous LiOH (1M, 1.44 mL) in THF (3 mL) was stirred for 2 hours. Aqueous HCl (1M, 2 mL) was added, and the mixture was extracted with ethyl acetate. The organic phase was washed with brine, dried (MgSO₄), and concentrated to give 2-(R,S)-benzyloxycarbonylamino-3-[4'-(1"-ᵗbutoxycarbonyl)cyclopentyl]benzenepropanoic acid (0.430 g, 96%).

2-(R,S)-Benzyloxycarbonylamino-3-[4'-(1"-ethyloxysulfonyl-1"-methyl)ethyl)benzene]propanoic acid Scheme 10

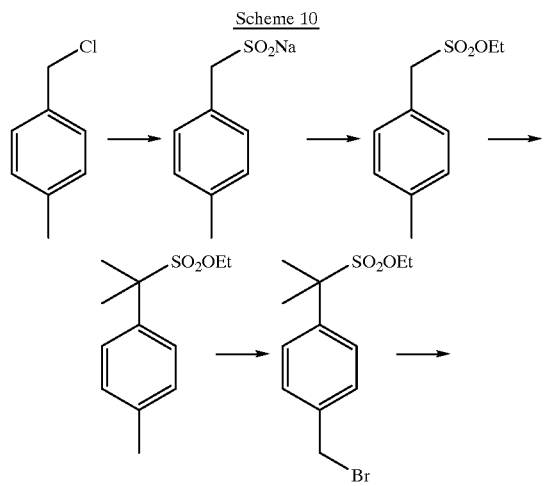

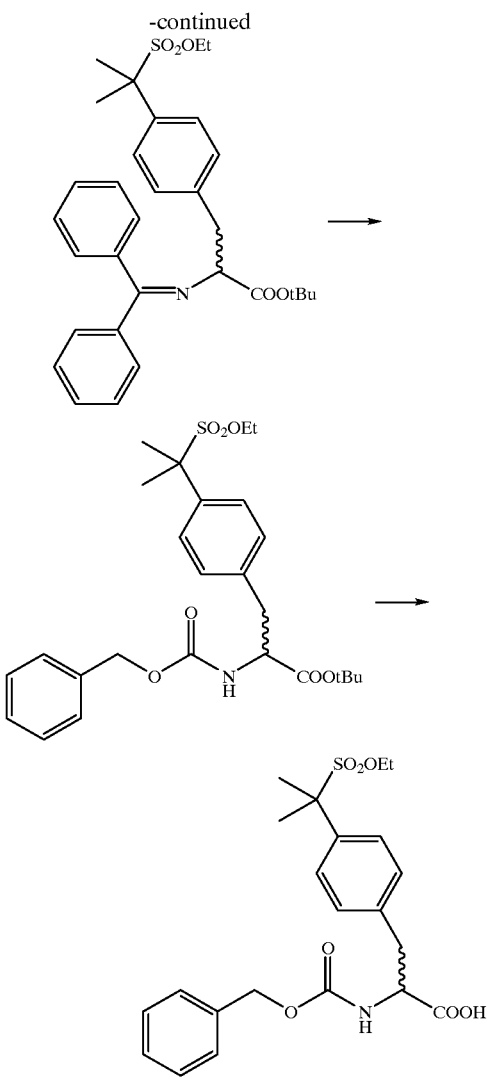

4-Methylphenylmethanesulfonic acid, sodium salt

To a solution of sodium sulfite (14.3 g, 113 mmol) in water (60 mL) was added 4-methylbenzyl chloride (15.0 mL, 1 13 mmol). The mixture was stirred under reflux for 12 hours, and cooled to rt. The precipitate was collected by filtration, and washed with water and ether to give 4-methylphenylmethanesulfonic acid sodium salt (12.5 g, 60 mmol, 53%).

Ethyl 4-methylphenylmethanesulfonate

To 4-methylphenylmethanesulfonic acid, sodium salt (9.22 g, 44.3 mmol) cooled on ice in a flask fitted with an overhead stirrer was added phosphorus pentachloride (9.22 g, 44.3 mmol) and phosphorus oxychloride (1.5 mL). The mixture was stirred for 2 hours at 0° C., and allowed to warm to rt. The phosphorus oxychloride was removed under vacuum, and the residue was cooled to −10° C. Ethanol (13 mL) was added, followed by pyridine (18 mL) added slowly over 2 hours. The mixture was left in the freezer overnight, and then allowed to warm to rt. Methylene chloride was added, the mixture was washed with 1N HCl and brine, and dried ($K_2CO_3$). Evaporation of the solvent followed by chromatography of the residue over silica gel (15% ethyl acetate/hexane) gave ethyl 4-methylphenylmethanesulfonate (3.13 g, 14.6 mmol, 33%).

Ethyl 1-methyl-1-(4-methylphenyl)ethanesulfonate

To a solution of butyllithium (2.5M in hexanes, 2.94 mL) in THF (3.5 mL) cooled to −60° C. was added ethyl 4-methylphenylmethanesulfonate (1.05 g, 4.91 mmol) in THF (5 mL). After 15 minutes, iodomethane (0.61 mL, 9.8 mmol) was added, and the mixture was stirred for 1 hour at −50 to −30° C. The mixture was recooled to −60° C., and further butyllithium (2.94 mL) and iodomethane (0.61 mL) were added. The reaction was quenched with aqueous ammonium chloride, and extracted with ether. The organic phase was dried ($K_2CO_3$), filtered and evaporated. Chromatography of the residue over silica gel (15% ethyl acetate/hexane) gave ethyl 1-methyl-1-(4-methylphenyl)ethanesulfonate (0.917 g, 3.79 mmol, 77%).

Ethyl 1-methyl-1-(4-bromomethylphenyl)ethanesulfonate

To a solution of ethyl 1-methyl-1-(4-methylphenyl)ethanesulfonate (0.458 g, 1.89 mmol) in carbon tetrachloride (8 mL) was added N-bromosuccinimide (0.370 g, 2.08 mmol) and benzoyl chloride (0.009 g). The mixture was heated under reflux for 1.5 hours, cooled to rt, and filtered. The filtrate was washed with aqueous sodium bicarbonate and brine, dried, filtered and evaporated to give crude ethyl 1-methyl-1-(4-bromomethylphenyl)ethanesulfonate (0.64 g, 100%) which was used directly in the next reaction.

2-(R,S)-Benzyloxycarbonylamino-3-[4'-(1"-ethyloxysulfonyl-1"-methyl)ethyl)benzene] propanoic acid To a solution of ethyl 1-methyl-1-(4-bromomethylphenyl) ethanesulfonate (0.64 g, 1.89 mol) and N-diphenylmethyleneglycine $^t$butyl ester (0.586 g 1.98 mmol) in THF (6.5 mL) cooled on ice was added sodium bis(trimethylsilyl)amide (2M in THF, 1.04 mL). After 30 minutes the solvent was evaporated, the residue was taken up in acetic acid (2 mL), water (2 mL) and methanol (4 mL), and stirred at rt for 4 hours. The methanol was evaporated, water was added, and the mixture was washed with hexane/ether 1/1 (2×20 mL). The organic phase was washed with water. The combined aqueous phase was cooled on ice, and adjusted to pH 7 with sodium bicarbonate. Dioxane was added followed by benzyl chloroformate (0.38 mL, 2.65 mmol) and the mixture was stirred coming to rt overnight. Water was added, and the mixture was acidified to pH 3 with 1N $H_2SO_4$. The mixture was extracted with ethyl acetate, and the organic phase was dried, filtered and evaporated. Chromatography of the residue over silica gel (10% to 20% ethyl acetate/hexane) gave crude 2-(R,S)-benzyloxycarbonylamino-3-[4'-(1"-ethyloxysulfonyl-1"-methyl)ethyl)benzene]propanoic acid $^t$butyl ester (0.645 g, 68%). To a solution of the crude ester in methylene chloride (9 mL) cooled on ice was added trifluoroacetic acid (1.5 mL). The mixture was stirred for 4 hours, warming to rt. The reaction was quenched with cold aqueous sodium bicarbonate, and extracted with methylene chloride. The solvent was evaporated, and chromatography of the residue over silica gel (methylene chloride to 10% methanol/methylene chloride) gave 2-(R,S)-benzyloxycarbonylamino-3-[4'-(1"-ethyloxysulfonyl-1"-methyl)ethyl)benzene]propanoic acid (0.396 g, 0.88 mmol, 69%).

While we have herein before presented a number of embodiments of this invention, it is apparent that our basic construction can be altered to provide other embodiments that utilize the processes and compositions of this invention. For example, obvious variations of the synthetic process steps and intermediates described and exemplified herein will be easily recognized by those of ordinary skill in the art. This application expressly envisions and extends to those obvious variations. It should be appreciated that the scope of this invention is defined by the following claims rather than by the specific embodiments that have been presented hereinabove by way of example.

What is claimed is:

1. A compound of the formula (I):

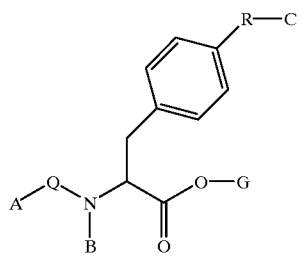

(I)

wherein:

A is selected from the group consisting of alkyl; alkenyl; alkynyl; alkoxy; cycloalkyl; cycloalkenyl; heterocyclyl selected from pyrrolyl and pyrrolinyl each heterocycyl is optionally partially or fully halogenated and optionally substituted with alkyl, hydroxyl, nitro, —COOH, —CO(lower alkoxy), —CO(lower alkyl), amino, alkylamino dialkylamino, alkoxy, —NCOH, —NCO(lower alkyl), —NSO$_2$—Ph(halo)$_{0-3}$, Ph, —O—Ph, naphthyl, —O—naphthyl, pyrrolyl and pyrrolyl subsituted with lower alkyl; and aryl; wherein said cycloalkyl, heterocyclyl or aryl is optionally linked to Q or N via an alkoxy, —O—, amino, lower alkyl, lower alkyl amino, carbonyl, amido, amido alkyl, alkoxycarbonyl, carbonylalkyloxy, cycloalkyl and heterocyclyl linker wherein the heterocyclyl is as hereinabove defined;

Q is selected from the group consisting of a bond, >C=O, >S(O)$_2$ and >C=S; wherein A and Q optionally form a nitrogen protecting group (NPG);

B is selected from the group consisting of H; lower alkyl and a nitrogen-protecting group;

G is selected from the group consisting of H or an oxygen-protecting group (OPG);

R is CR$_1$R$_2$ wherein R$_1$ is H, alkyl, or alkoxy and R$_2$ is OH, alkyl or alkoxy, and wherein R$_1$ and R$_2$ may be connected to form a ring of between three and 6 members if R$_1$ is alkyl or alkyloxy;

C is an acidic functionality selected from carboxyl, sulfonyl and the ester derivates thereof wherein C is optionally covalently attached to an OPG and the pharmaceutically acceptable salts thereof.

2. The compound according to claim 1 wherein:

B is hydrogen;

R is CHOH, C(CH$_3$)OH, C(CH$_3$)$_2$, C(CH$_2$CH$_3$)$_2$, cyclopropyl, cyclopentyl or CHCH$_3$.

3. The compound according to claim 2 wherein R is —C(CH$_3$)$_2$— and C is a carboxyl group.

4. A pharmaceutical composition comprising a phoshotyrosine mimic compound of the formula (I):

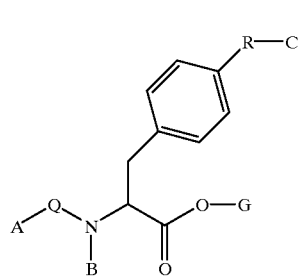

(I)

wherein:

A is selected from the group consisting of alkyl; alkenyl; alkynyl; alkoxy; cycloalkyl; cycloalkenyl; heterocyclyl selected from pyrrolyl and pyrrolinyl each heterocycyl is optionally partially or fully halogenated and optionally substituted with alkyl, hydroxyl, nitro, —COOH, —CO(lower alkoxy), —CO(lower alkyl), amino, alkylamino, dialkylamino, alkoxy, —NCOH, —NCO(lower alkyl), —NSO$_2$—Ph(halo)$_{0-3}$, Ph, —O—Ph, naphthyl, —O—naphthyl, pyrrolyl and pyrrolyl subsituted with lower alkyl; and aryl; wherein said cycloalkyl, heterocyclyl or aryl is optionally linked to Q or N via an alkoxy, —O—, amino, lower alkyl, lower alkyl amino, carbonyl, amido, amido alkyl, alkoxycarbonyl, carbonylalkyloxy, cycloalkyl and heterocyclyl linker wherein the heterocyclyl is as hereinabove defined;

Q is selected from the group consisting of a bond, >C=O, >S(O)$_2$ and >C=S; wherein A and Q optionally form a nitrogen protecting group (NPG);

B is selected from the group consisting of H; lower alkyl and a nitrogen-protecting group;

G is selected from the group consisting of H or an oxygen-protecting group (OPG);

R is CR$_1$R$_2$ wherein R$_1$ is H, alkyl, or alkoxy and R$_2$ is OH, alkyl or alkoxy, and wherein R$_1$ and R$_2$ may be connected to form a ring of between three and 6 members if R$_1$ is alkyl or alkyloxy;

C is an acidic functionality selected from carboxyl, sulfonyl and the ester derivates thereof wherein C is optionally covalently attached to an OPG and wherein the pharmaceutical composition is capable of inhibiting binding of tyrosine kinase-dependent regulatory proteins.

5. The pharmaceutical composition according to claim 4 wherein:

B is hydrogen;

R is CHOH, C(CH$_3$)OH, C(CH$_3$)$_2$, C(CH$_2$CH$_3$)$_2$, cyclopropyl, cyclopentyl or CHCH$_3$.

6. The pharmaceutical composition according to claim 5 wherein R is —C(CH$_3$)$_2$— and C is a carboxyl group.

7. A method of treating a neoplastic disease or chronic inflammatory disease, said method comprising administering to a patient in need thereof a pharmaceutically effective amount of a compound according to claim 1.

8. The method according to claim 7 wherein the neoplastic disease is selected from acute lymphocytic leukemia, acute lymphoblastic leukemia, chronic lymphocytic leukemia, acute myloblastic leukemia, chronic mylocytic leukemia, carcinoma, adenocarcinoma, sarcoma, malignant melanoma, mixed types of neoplasias selected from carcinosarcoma, lymphoid tissue type, folicullar reticulum, cell sarcoma and Hodgkin's disease, neuroblastoma, cerebral malaria, capillary leak syndrome and hematological malignancies.

9. The method according to claim 7 wherein the inflammatory diseases are selected from rheumatoid arthritis, multiple sclerosis, Guillain-Barre syndrome, Crohn's disease, ulcerative colitis, psoriasis, graft versus host disease, lupus erythematosus and insulin-dependent diabetes mellitus.

10. A method of inhibiting the binding of tyrosine kinase-dependent regulatory proteins which comprises administering to a subject in need of such treatment pharmaceutically effective amount of a phosphotyrosine mimic containing composition according to claim 4.

* * * * *